United States Patent [19]

Sih

[11] 4,259,529

[45] Mar. 31, 1981

[54] 2-DECARBOXY-2-HYDROXYMETHYL-19,20-DIDEHYDRO-13,14-DIHYDRO-PG$_1$ COMPOUNDS

[75] Inventor: John C. Sih, Kalamazoo, Mich.

[73] Assignee: The Upjohn Company, Kalamazoo, Mich.

[21] Appl. No.: 85,626

[22] Filed: Oct. 17, 1979

Related U.S. Application Data

[62] Division of Ser. No. 26,066, Apr. 2, 1979.

[51] Int. Cl.$^3$ ............................................. C07C 177/00
[52] U.S. Cl. ................................... 568/379; 568/330; 568/646; 568/670; 568/807; 568/838
[58] Field of Search ...................... 260/590 C, 586 R; 568/646, 670, 807, 838, 330, 379

[56] References Cited

FOREIGN PATENT DOCUMENTS 2635985 2/1978 Fed. Rep. of Germany ........... 560/121

*Primary Examiner*—Robert Gerstl
*Attorney, Agent, or Firm*—Robert A. Armitage

[57] ABSTRACT

The present invention provides novel 2-decarboxy-2-hydroxymethyl-19,20-didehydro-13,14-dihydro-PG$_1$ compounds methods for their preparation and pharmacological use for the induction of prostaglandin-like effect.

29 Claims, No Drawings

2-DECARBOXY-2-HYDROXYMETHYL-19,20-DIDEHYDRO-13,14-DIHYDRO-PG₁ COMPOUNDS

CROSS REFERENCE TO RELATED APPLICATIONS

The present application is a division of Ser. No. 26,066, filed Apr. 2, 1979, pending issuance as a U.S. Patent.

BACKGROUND OF THE INVENTION

The present invention relates to novel prostaglandin analogs. Particularly, these compounds are analogs of the prostaglandins wherein the C-20 - C-19 position is unsaturated, i.e., 19,20-didehydro-PG compounds. Most particularly, the present invention relates to novel 2-decarboxy-2-hydroxymethyl-19,20-didehydro-13,14-dihydro-PG₁ compounds, a disclosure of the preparation and use of which is incorporated here by reference from U.S. Pat. 4,228,104 filed Apr. 2, 1979.

PRIOR ART

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 26,066.

SUMMARY OF THE INVENTION

The present invention particularly provides:
A compound of the formula

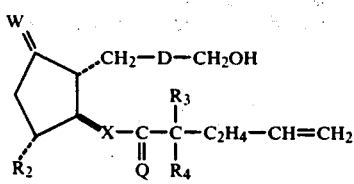

wherein D is:
(1) —(CH₂)₃—(CH₂)_g—CH₂—,
(2) —(CH₂)₃—CH₂—CF₂—,
(3) —(CH₂)₃—O—CH₂—,
(4) —(CH₂)₂—O—(CH₂)₂—,
(5) —CH₂—O—(CH₂)₃—,

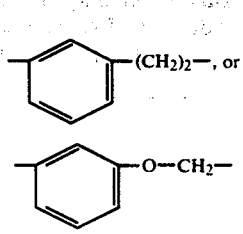 (6)

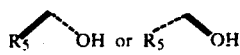 (7)

wherein g is zero, one, two, or three; wherein Q is

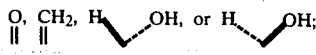

wherein R₅ is hydrogen or methyl, wherein R₂ is hydrogen, hydroxyl, or hydroxymethyl; wherein R₃ and R₄ are hydrogen, methyl, or fluoro, being the same or different, with the proviso that one of R₃ and R₄ is fluoro only when the other is hydrogen or fluoro; wherein W is $$\overset{O}{\underset{\|}{}}, \overset{CH_2}{\underset{\|}{}}, H\diagdown\diagup OH, \text{ or } H\diagdown\diagup OH;$$

and wherein X is —CH₂CH₂—.

Specific embodiments of the present invention include
2-decarboxy-2-hydroxymethyl-13,14-dihydro-19,20-didehydro-PGF₁,
2-decarboxy-2-hydroxymethyl-11-deoxy-13,14-dihydro-19,20-didehydro-PGF₁α,
2-decarboxy-2-hydroxymethyl-11-deoxy-11α-hydroxymethyl-13,14-dihydro-19,20-didehydro-PGF₁α,
2-decarboxy-2-hydroxymethyl-13,14-dihydro-19,20-didehydro-PGF₂β,
2-decarboxy-2-hydroxymethyl-11-deoxy-13,14-dihydro-19,20-didehydro-PGF₁β,
2-decarboxy-2-hydroxymethyl-11-deoxy-11α-hydroxymethyl-13,14-dihydro-19,20-didehydro-PGF₁β,
2-decarboxy-2-hydroxymethyl-13,14-dihydro-19,20-didehydro-PGE₁,
2-decarboxy-2-hydroxymethyl-11-deoxy-13,14-dihydro-19,20-didehydro-PGE₁,
2-decarboxy-2-hydroxymethyl-11-deoxy-11α-hydroxymethyl-13,14-dihydro-19,20-didehydro-PGE₁,
2-decarboxy-2-hydroxymethyl-9-deoxo-9-methylene-11-deoxy-1,3,14-dihydro-19,20-didehydro-PGE₁,
2-decarboxy-2-hydroxymethyl-9-deoxo-9-methylene-11-deoxy-11α-hydroxymethyl-13,14-dihydro-19,20-didehydro-PGE₁.

The compounds of the present invention are particularly useful for inducing prostaglandin-like biological effects, as is described in U.S. Ser. No. 26,066. Uses of compounds in accordance with the present invention include, therefore, anti-asthmatic indication.

I claim:
1. A compound of the formula

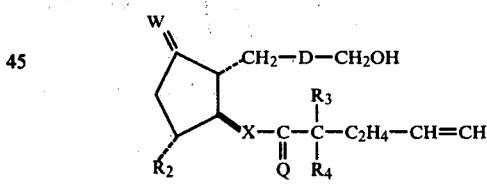

wherein D is
(1) —(CH₂)₃—(CH₂)_g—CH₂—,
(2) —(CH₂)₃—CH₂—CF₂—,
(3) —(CH₂)₃—O—CH₂—,
(4) —(CH₂)₂—O—(CH₂)₂—,
(5) —CH₂—O—(CH₂)₃—,

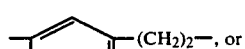 (6)

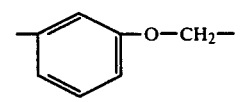 (7)

wherein g is zero, one, two, or three; wherein Q is

wherein R$_5$ is hydrogen or methyl, wherein R$_2$ is hydrogen, hydroxyl, or hydroxymethyl; wherein R$_3$ and R$_4$ are hydrogen, methyl, or fluoro, being the same or different, with the proviso that one of R$_3$ and R$_4$ is fluoro only when the other is hydrogen or fluoro; wherein W is

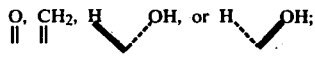

and wherein X is —CH$_2$CH$_2$—.

2. A compound according to claim 1, wherein D is —(CH$_2$)$_3$—(CH$_2$)$_g$—CH$_2$—, wherein g is zero, one, two or three.

3. A compound according to claim 2, wherein g is one.

4. A compound according to claim 3, wherein W is

5. A compound according to claim 4, wherein R$_2$ is hydroxyl.

6. 2-Decarboxy-2-hydroxymethyl-13,14-dihydro-19,20-didehydro-PGF$_{1\alpha}$, a compound according to claim 5.

7. A compound according to claim 4, wherein R$_2$ is hydrogen.

8. 2-Decarboxy-2-hydroxymethyl-11-deoxy-13,14-dihydro-19,20-didehydro-PGF$_{1\alpha}$, a compound according to claim 7.

9. A compound according to claim 4, wherein R$_2$ is hydroxymethyl.

10. 2-Decarboxy-2-hydroxymethyl-11-deoxy-11α-hydroxymethyl-13,14-dihydro-19,20-didehydro-PGF$_{1\alpha}$, a compound according to claim 9.

11. A compound according to claim 3, wherein W is

12. A compound according to claim 11, wherein R$_2$ is hydroxyl.

13. 2-Decarboxy-2-hydroxymethyl-13,14-dihydro-19,20-didehydro-PGF$_{2\beta}$, a compound according to claim 12.

14. A compound according to claim 11, wherein R$_2$ is hydrogen.

15. 2-Decarboxy-2-hydroxymethyl-11-deoxy-13,14-dihydro-19,20-didehydro-PGF$_{1\beta}$, a compound according to claim 14.

16. A compound according to claim 14, wherein R$_2$ is hydroxymethyl.

17. 2-Decarboxy-2-hydroxymethyl-11-deoxy-11α-hydroxy-methyl-13,14-dihydro-19,20-didehydro-PGF$_{1\beta}$, a compound according to claim 16.

18. A compound according to claim 3, wherein W is $$\overset{O}{\underset{\|}{\phantom{X}}}$$

19. A compound according to claim 18, wherein R$_2$ is hydroxyl.

20. 2-Decarboxy-2-hydroxymethyl-13,14-dihydro-19,20-didehydro-PGE$_1$, a compound according to claim 19.

21. A compound according to claim 18, wherein R$_2$ is hydrogen.

22. 2-Decarboxy-2-hydroxymethyl-11-deoxy-13,14-dihydro-19,20-didehydro-PGE$_1$, a compound according to claim 21.

23. A compound according to claim 18, wherein R$_2$ is hydroxymethyl.

24. 2-Decarboxy-2-hydroxymethyl-11-deoxy-11α-hydroxymethyl-13,14-dihydro-19,20-didehydro-PGE$_1$, a compound according to claim 23.

25. A compound according to claim 3, wherein W is $$\overset{CH_2}{\underset{\|}{\phantom{X}}}$$

26. A compound according to claim 25, wherein R$_2$ is hydroxyl.

27. 2-Decarboxy-2-hydroxymethyl-9-deoxo-9-methylene-13,14-dihydro-19,20-didehydro-PGE$_1$, a compound according to claim 26.

28. A compound according to claim 25, wherein R$_2$ is hydroxymethyl.

29. 2-Decarboxy-2-hydroxymethyl-9-deoxo-9-methylene-11-deoxy-11α-hydroxymethyl-13,14-dihydro-19,20-didehydro-PGE$_1$, a compound according to claim 28.

* * * * *

UNITED STATES PATENT OFFICE
CERTIFICATE OF CORRECTION

Patent No. 4,259,529　　　　　　　　Dated 31 March 1981

Inventor(s) John C. Sih

It is certified that error appears in the above-identified patent and that said Letters Patent are hereby corrected as shown below:

"Related U.S. Application Data" should read -- Division of Ser. No. 26,066, Apr. 2, 1979, Pat. No. 4,243,611 --;

Column 1, lines 8+9, "pending issuance as a U.S. Patent" should read -- now U.S. Patent 4,243,611 --; line 29, "U.S. Ser. No. 26,066" should read -- U.S. Pat. No. 4,243,611 --;

Column 2, line 37, "U.S. Ser. No. 26,066" should read -- U.S. Pat. No. 4,243,611 --;

Column 4, line 2, "$PGF_2\beta$," should read -- $PGF_1\beta$, --; line 9, "according to claim 14" should read -- according to claim 11 --.

Signed and Sealed this

Eighth Day of September 1981

[SEAL]

Attest:

GERALD J. MOSSINGHOFF

Attesting Officer　　　Commissioner of Patents and Trademarks